(12) United States Patent
Schuchardt et al.

(10) Patent No.: US 11,033,376 B2
(45) Date of Patent: *Jun. 15, 2021

(54) CUFF FOR AN ARTIFICIAL URINARY SPHINCTER SYSTEM

(71) Applicant: Coloplast A/S, Humlebaek (DK)

(72) Inventors: Sarah J Schuchardt, Minneapolis, MN (US); Jon Cornell, Savage, MN (US)

(73) Assignee: Coloplast A/S, Humlebaek (DK)

( * ) Notice: Subject to any disclaimer, the term of this patent is extended or adjusted under 35 U.S.C. 154(b) by 70 days.

This patent is subject to a terminal disclaimer.

(21) Appl. No.: 16/255,837

(22) Filed: Jan. 24, 2019

(65) Prior Publication Data

US 2019/0151063 A1    May 23, 2019

Related U.S. Application Data

(63) Continuation of application No. 13/945,928, filed on Jul. 19, 2013, now Pat. No. 10,226,317.

(30) Foreign Application Priority Data

Jul. 24, 2013   (EP) ...................................... 13177795
Jul. 24, 2013   (EP) ...................................... 15188189

(51) Int. Cl.
*A61F 2/00*        (2006.01)
(52) U.S. Cl.
CPC .................................... *A61F 2/004* (2013.01)

(58) Field of Classification Search
CPC ........ A61F 2/00; A61F 2/0004; A61F 2/0031; A61F 2/0036; A61F 2/004; A61F 2/04; A61F 2/042; A61F 17/12
See application file for complete search history.

(56) References Cited

U.S. PATENT DOCUMENTS

| | | | | |
|---|---|---|---|---|
| 4,019,499 A | * | 4/1977 | Fitzgerald | A61F 2/004 600/30 |
| 4,222,377 A | * | 9/1980 | Burton | A61F 2/004 600/31 |
| 4,632,114 A | * | 12/1986 | Todd | A61F 2/004 128/DIG. 25 |
| 2008/0243152 A1 | * | 10/2008 | Paganon | A61F 5/0066 606/157 |

* cited by examiner

*Primary Examiner* — Carrie R Dorna
(74) *Attorney, Agent, or Firm* — Coloplast Corp., Coloplast A/S; Nick Baumann (57) ABSTRACT

A cuff for an artificial urinary sphincter (AUS) system includes an interior wall that is smooth and characterized by an absence of creases, an exterior wall that provides the cuff with a backboard adapted to support movement of the interior wall, and endwalls. A cavity is located between the interior wall, the exterior wall, and the pair of endwalls and is adapted to contain a liquid. Liquid in the cavity is maintained at an equilibrium pressure that is selected to displace the interior wall and maintain the cuff in a closed position around the urethra to provide the user with urinary continence.

2 Claims, 9 Drawing Sheets

CUFF FOR AN ARTIFICIAL URINARY SPHINCTER SYSTEM

BACKGROUND

Urinary incontinence affects about 200 million people worldwide and about 25 million people in the US. Urinary incontinence is generally more prevalent in women than in men.

Urinary incontinence in women can be associated with a prolapse of one or more pelvic organs, which can arise from a weakness in the tissues/muscle of the pelvic floor. Urinary incontinence in men can arise after surgical treatment of the prostate glade, which treatment can include removal or weakening of the prostatic sphincter associated with the urinary urethra.

One treatment for urinary incontinence includes placing an artificial sphincter around a portion of the urethra. The artificial sphincter has a closed position that selectively prevents the flow of urine through the urethra, thus providing the user with a comfortable, continent state. The artificial sphincter can be activated to an open position by the user, which opens the urethra and allows the user to selectively pass urine.

Surgeons and patients would welcome advances in the treatment of urinary incontinence.

SUMMARY

One aspect provides an artificial urinary sphincter system having a pressure reservoir attachable to a pump and a conduit attachable between the pump and a cuff. The cuff is formed as a one-piece monolithic polymer structure that is substantially circular in radial cross-section. The cuff has an interior wall connected by a pair of opposing end walls to an exterior wall. The cuff includes a closed cavity located between the interior wall and the exterior wall and between the pair of opposing end walls. The one-piece monolithic polymer structure has a part line that is formed by a first face of the cuff that is separable from a second face of the cuff to allow the first face to be separated from the second face for placement of the cuff around a urethra of a user. The conduit is attachable to a connector that is attached to the exterior wall of the cuff adjacent to one of the first face or the second face. The connector communicates with the closed cavity. A thickness of the interior wall is less than a thickness of the exterior wall and less than a thickness of each of the pair of opposing end walls.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Tissue includes soft tissue, which includes dermal tissue, sub-dermal tissue, ligaments, tendons, or membranes. As employed in this specification, the term "tissue" does not include bone.

As employed in this specification, the term "end" means endmost or the very end point of the subject being described, and the term "end portion" means that segment that is immediately adjacent to the end of the subject being described.

Figure 1A:
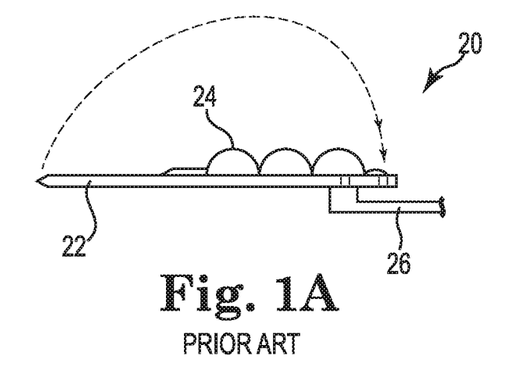
FIG. 1A is a side view of a prior art cuff and FIG. 1B is a perspective view of an artificial urinary sphincter (AUS) system with the prior art cuff.
Figure 1B:
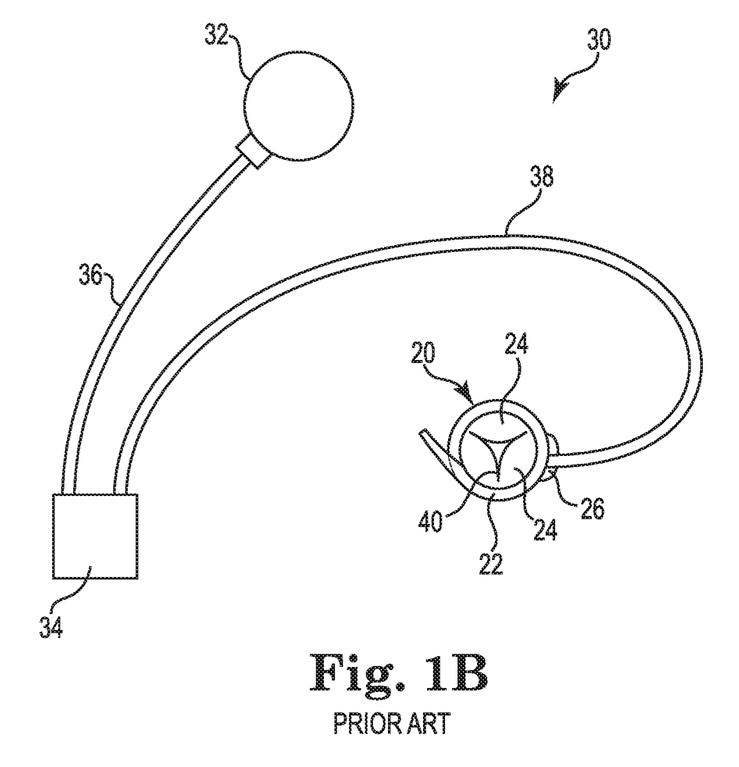

FIG. 1A is a side view of a prior art cuff 20 and FIG. 1B is a perspective view of an artificial urinary sphincter (AUS) system 30 including the prior art cuff 20. The cuff 20 includes a backing 22, an inflatable balloon 24 attached to the backing 22, and a conduit that communicates with the inflatable balloon 24. The backing 22 is generally inextensible and configured to retain the cuff 20 in position as the inflatable balloon 24 is inflated to coapt the urethra.

The system 30 includes a pressure-regulating reservoir 32 attached to a pump 34 by tubing 36 with the cuff 20 attached to the pump 34 by separate tubing 38. The pump 34 is implantable in the scrotum of a male user. The pressure-regulating reservoir 32 is implantable in the prevesical space posterior the rectus fascia and the linea alba. The system 30 is filled with liquid (e.g., saline) to provide a liquid-filled closed system maintained at an equilibrium pressure that is selected to close the cuff 20 around the urethra. When the user wishes to void, he squeezes and releases the pump 34 several times to move the liquid from the cuff 20 into the pressure-regulating reservoir 32. The cuff 20 "deflates" and opens, which allows the urethra to open and pass urine. The pressure-regulating reservoir 32, having been pressurized to a pressure above the equilibrium pressure by action of the pump 34, eventually returns to the equilibrium pressure over the course of several minutes to again inflate the cuff 20 and coapt the urethra.

With reference to FIG. 1B, the cuff 20 is illustrated with one end wrapped around to meet the second end to allow the cuff 20 to surround the urethra. When the generally rectangular cuff 20 (FIG. 1A) is formed around the urethra, the inflatable balloons 24 become bunched together and unavoidably become creased. The bunching together of the inflatable balloons 24 can lead to the development of regions of stress 40 in the balloon-forming layer. The regions of stress 40 can potentially cause the balloon-forming layer to fail, resulting in a leakage in the system 20. The bunching together of the inflatable balloons 24 also has the potential to undesirably pinch or erode the sensitive tissue of the urethra.

Embodiments described in this application provide a cuff that is formed as a one-piece monolithic structure that is substantially circular in radial cross-section. The one-piece monolithic structure has a smooth interior wall providing an absence of creases and an absence of concentrated stress regions on an interior surface of the cuff. The one-piece monolithic structure includes a closed cavity that is filled with liquid to inflate and deflate the cuff. Embodiments provide an interior wall having a thickness that is less than a thickness of the exterior wall of the monolithic cuff. In this manner, the exterior wall supports the cuff (or provides a supporting backbone) as the cuff is inflated, which allows the interior wall to expand to coapt the urethra. The smooth interior wall inflates evenly and uniformly to reduce the formation of stress points that can undesirably lead to leakage of the saline through the cuff, and ensures improved coaptation of the urethra with reduced or no pinching of the urethral tissue.

Figure 2:
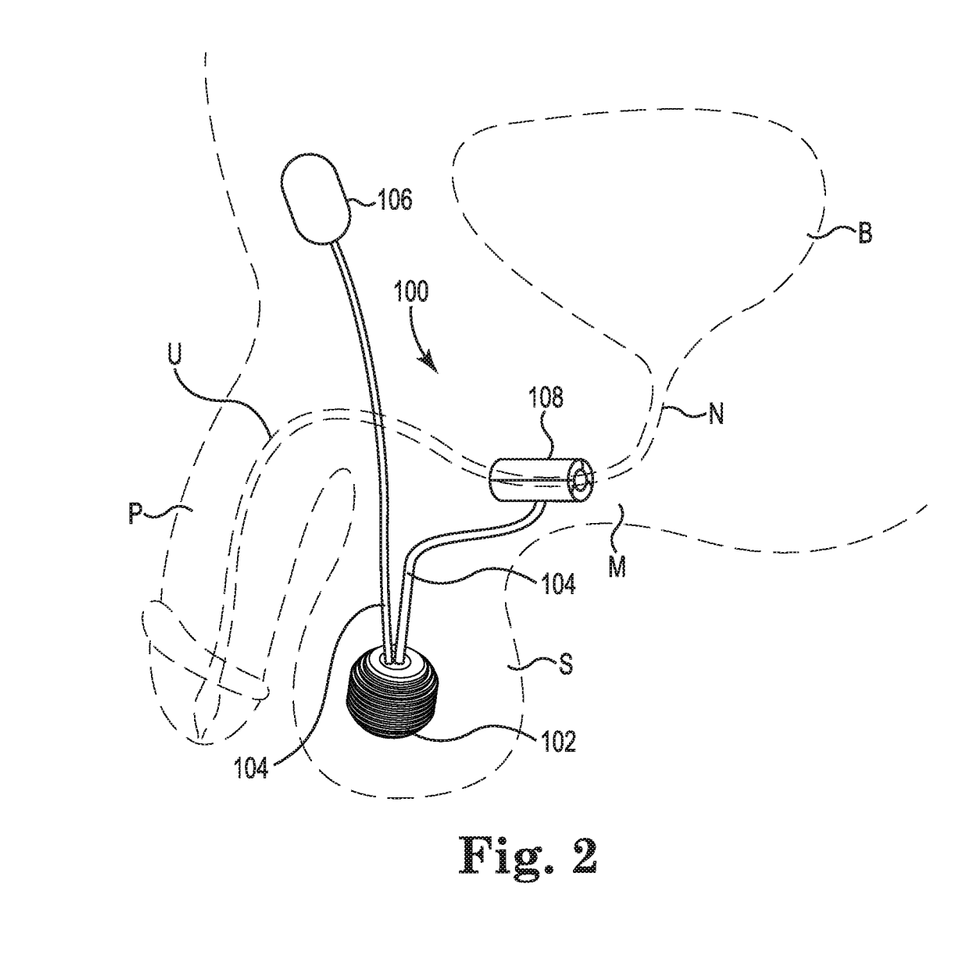
FIG. 2 is a perspective view of one embodiment of an AUS system implanted in the environment of the male urogenital region.

FIG. 2 is a perspective view of one embodiment of an artificial urinary sphincter (AUS) system 100 illustrated as implanted in the environment of the male urogenital region. The AUS system 100 includes a pump 102 attachable with tubing 104 between a pressure regulating reservoir 106 and a cuff 108.

The pump 102 is typically implanted within the scrotum S, which provides convenient access to the pump 102 by a male user. Other locations for placement of the pump 102 are also acceptable, for example within the labia as determined by the gender of the user.

The pump 102 is operable to inflate the cuff 108. One suitable pump 102 is the suction style pump bulb as illustrated that operates to remove liquid from the cuff 108 and transport the liquid into the reservoir 106. Other suitable pump mechanisms are also acceptable, including electromechanical pumps, electronic pumps, button-style displacement pumps, and the like.

The tubing 104 is provided in a kink resistant form and includes some style of connector that allows segments of the tubing 104 to be attached to the system components (the reservoir 106 and the cuff 108) after the system 100 is primed with liquid. The tubing 104 is generally a thin-walled tube that is attachable between the pump 102 and the reservoir 106, and between the pump 102 and the cuff 108. In one embodiment, the tubing 104 is separate from the pump 102 and separate from the reservoir 106/cuff 108 and connects to these components through a locking mechanism, such as a quick connector or other suitable snap-fit connector.

The reservoir 106 is sized to retain a volume of liquid at an equilibrium pressure that is selected to inflate the cuff 108 for coaptation of the urethra. The reservoir 106 maintains the pressure in the closed system 100 after the tubing 104 is connected between the components.

The cuff 108 is implanted around the bulbous urethra or around the portion of the urethra descending from the bladder neck N. The cuff 108 is sized to allow placement as close to the bladder B as possible (desired by some surgeons), or positioned distal the bladder neck N as suitably determined by the attending surgeon. As illustrated in FIG. 2, the cuff 108 is implanted around the urethra U at a location where the urethra U transitions from a vertical orientation communicating with the bladder B to a horizontal orientation extending to the penis P, which desirably corresponds to the area of the urogenital region associated with an increased level of muscle M mass.

Figure 3:
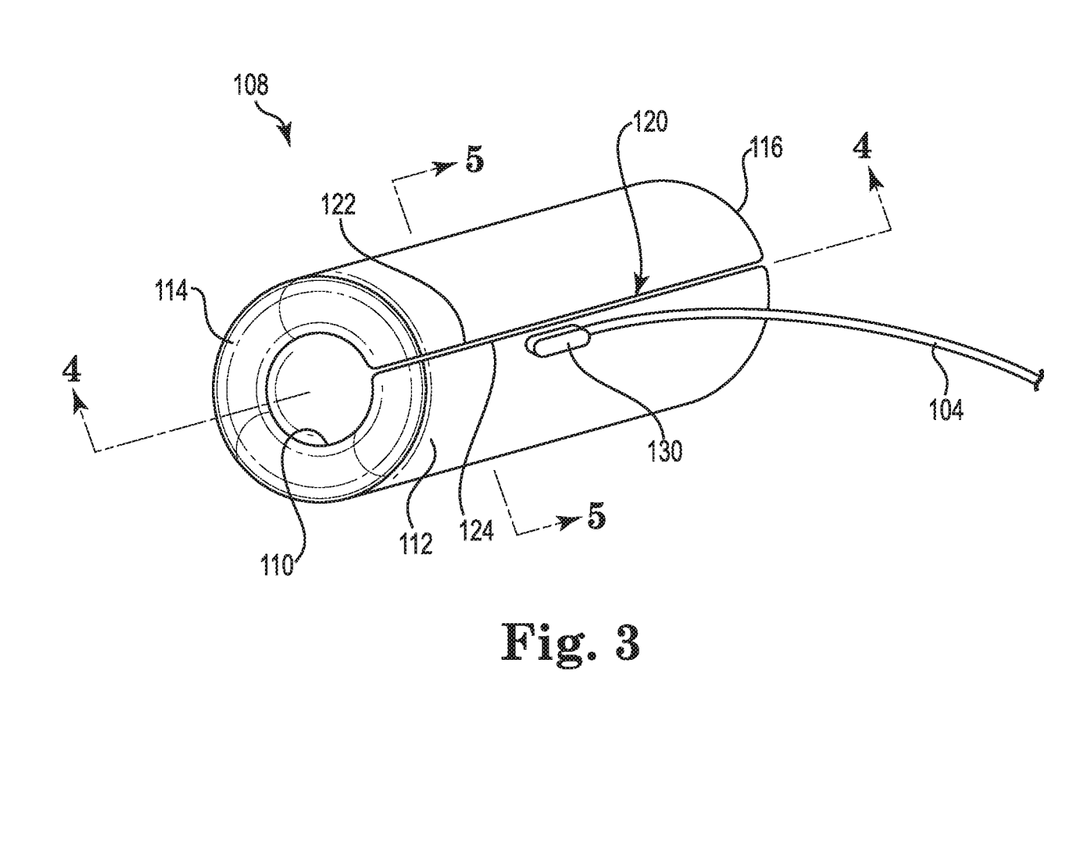
FIG. 3 is a perspective view of one embodiment of a cuff of the AUS system illustrated in FIG. 2.

FIG. 3 is a perspective view of one embodiment of the cuff 108. The cuff 108 is formed as a one-piece monolithic polymer structure that is substantially circular in radial cross-section (see FIG. 5).

The cuff 108 includes an interior wall 110 connected by a pair of opposing end walls 114, 116 to an exterior wall 112.

The cuff 108 includes a part line 120 formed longitudinally in an axial direction between the ends 114, 116. The part line 120 is formed by a first face 122 of the cuff 108 that is adjacent to or in contact with a second face 124 of the cuff 108. The part line 120 allows the cuff 108 to be "opened" for positioning around the urethra by separating the first face 122 from the second face 124. When the cuff 108 is implanted (or in its rest state), the first face 122 touches or is very close to the second face 124 such that the cuff 108 maintains its circular cross-sectional shape.

The cuff 108 includes a connector 130 that is in fluid communication with a cavity formed between the interior wall 110 and the exterior wall 112. The connector 130 is attached to the tubing 104 that extends to the pump 102 (FIG. 2). When the cuff 108 is implanted into a patient, the part line 120 is opened to secure the cuff 108 around the urethra. It is desirable for the surgeon to have access to the connector 130 after the cuff 108 is implanted, and for this reason the connector 130 is attached to the exterior wall 112 adjacent to the second face 124 of the part line 120. After implantation, the part line 120 will be oriented inferior to the urethra (standing position, or anterior the urethra) between the urethra and the perineum; positioning the connector 130 near the part line 120 provides the surgeon with optimal access to the connector 130.

In one embodiment, the lengths of the walls 110, 112 are about equal to the diameter of the cuff 108 such that the cuff 108 is "donut" shaped or in the shape of a torus. In one embodiment, the lengths of the walls 110, 112 are substantially greater than the diameter of the cuff 108 such that the cuff 108 is cylindrical in shape.

The cuff 108 is fabricated as a one-piece monolithic structure and is so configured that the interior wall 110 is smooth and wrinkle free in both the axial direction and in the radial direction around the cuff 108. Suitable fabrication processes for forming the cuff 108 include polymer molding, injection molding, lost wax molding, machining, three-dimensional printing, and other forms of forming an integrated one-piece structure. Suitable material for fabricating the cuff 108 includes polymers suitable for use in the fabrication process above, including silicone, polyurethane, polybutylene, and blends and mixtures of some or all of these materials.

Figure 4:
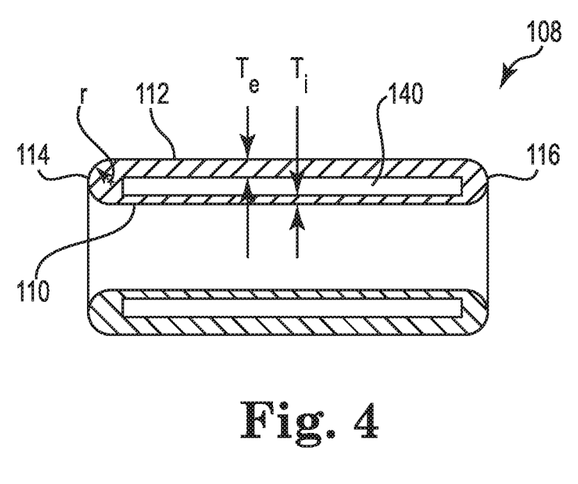
FIG. 4 is in axial cross-sectional view of the cuff illustrated in FIG. 3.
Figure 5:
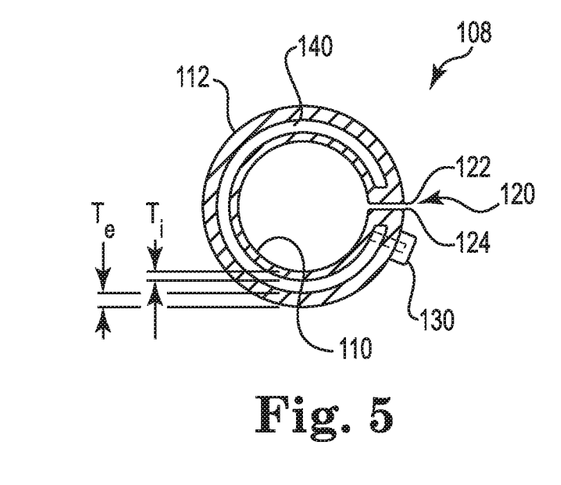
FIG. 5 is a radial cross-sectional view of the cuff illustrated in FIG. 3.

FIG. 4 is an axial cross-sectional view and FIG. 5 is a radial cross-sectional view of the cuff 108. The cuff 108 is an inflatable cuff and includes a closed cavity 140 formed between the interior wall 110, the exterior wall 112, and the end walls 114, 116. The closed cavity 140 communicates with the pump 102 and the reservoir 106 (FIG. 2) through the connector 130. The interior wall 110 is configured to expand inward relative to the cuff 108 when the liquid in the closed cavity 140 is pressurized by the pressure within the pressure regulating reservoir 106 (FIG. 2). In one embodiment, the interior wall 110 has a thickness Ti that is less than the thickness Te of the exterior wall 112. In one embodiment, the interior wall 110 has a thickness Ti that is less than the thickness Te of the exterior wall 112 and less than a thickness of the end walls 114, 116. In one embodiment, the thickness Ti of the interior wall 110 is less than one half of the thickness Te of the exterior wall.

FIG. 4 illustrates an embodiment having curved end walls 114, 116. In one embodiment, the end walls 114, 116 are formed by a constant radius r curvature. The axial cross-sectional view illustrated in FIG. 4 illustrates that the cuff 108 is cylindrical and non-circular in its axial direction, which provides a length that coapts a greater length of urethra compared to a donut shaped cuff. Both the interior wall 110 and the exterior wall 112 are substantially smooth in the axial direction and characterized by an absence of creases and an absence of folds. It is desirable that the cuff 108 is fabricated in a shape that represents the form that will be used when the cuff 108 is implanted. Embodiments provide a cuff that is pre-stressed when fabricated to maintain a substantially circular radial cross-sectional shape having a smooth interior wall.

Figure 6:
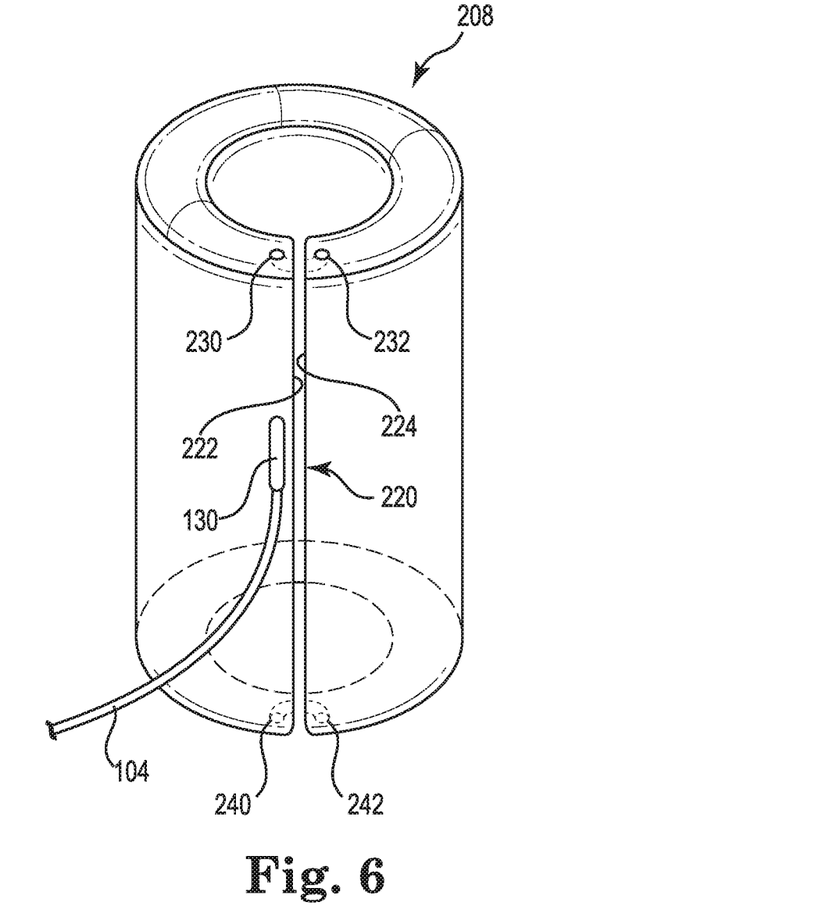
FIG. 6 is a perspective view of one embodiment of a cuff suitable for use with the AUS system illustrated in FIG. 2.

FIG. 6 is a perspective view of one embodiment of a cuff 208. The cuff 208 is similar to the cuff 108 described above and is fabricated as a one-piece monolithic polymer structure with a part line 220 and the connector 130 communicating with the internal closed cavity (not shown). The cuff 208 includes a closure mechanism provided by a first suture hole 230 that is formed in the end of the cuff 208 and extending through the first face 222 and a second suture hole 232 that is formed in the end of the cuff 208 and extending through the second face 224. The suture holes 230, 232 are provided to allow the surgeon to place a suture through the holes 230, 232 to retract and hold the opposing faces 222, 224 together. In one embodiment, a first set of suture holes 230, 232 is provided on a first end of the cuff 208 and a second set of suture holes 240, 242 is provided on the opposing end of the cuff 208.

Figure 7:
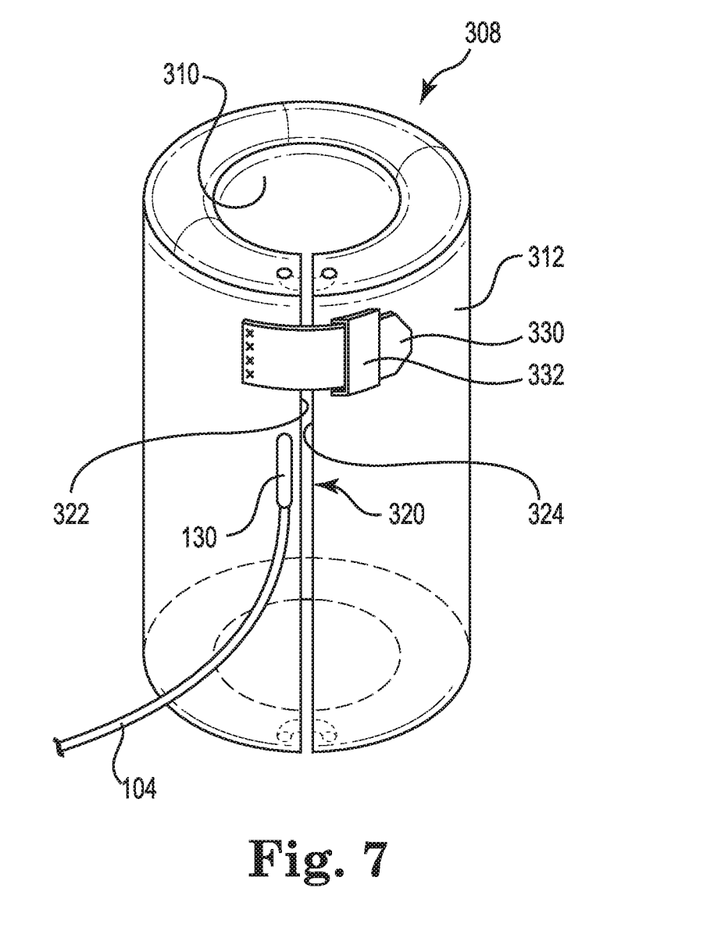
FIG. 7 is a perspective view of one embodiment of a cuff suitable for use with the AUS system illustrated in FIG. 2.

FIG. 7 is a perspective view of one embodiment of a cuff 308. The cuff 308 is similar to the cuff 108 described above and is fabricated as a one-piece monolithic polymer structure with a part line 320 and the connector 130 communicating with the closed cavity (not shown). The cuff 308 is fabricated to include a closure mechanism provided by a tongue 330 attached to the exterior wall 312 adjacent to, for example, the first face 322 of the part line 320 and a keeper 332 attached to the exterior wall 312 adjacent to the second face 324 of the part line 320. The tongue 330 is insertable through the keeper 332 to secure the cuff 308 around the urethra. In one embodiment, the tongue 330 includes a set of teeth that engage with a ratchet formed on the inside of the keeper 332. Other forms of retaining the tongue 330 inserted into the keeper 332 are also acceptable.

Figure 8:
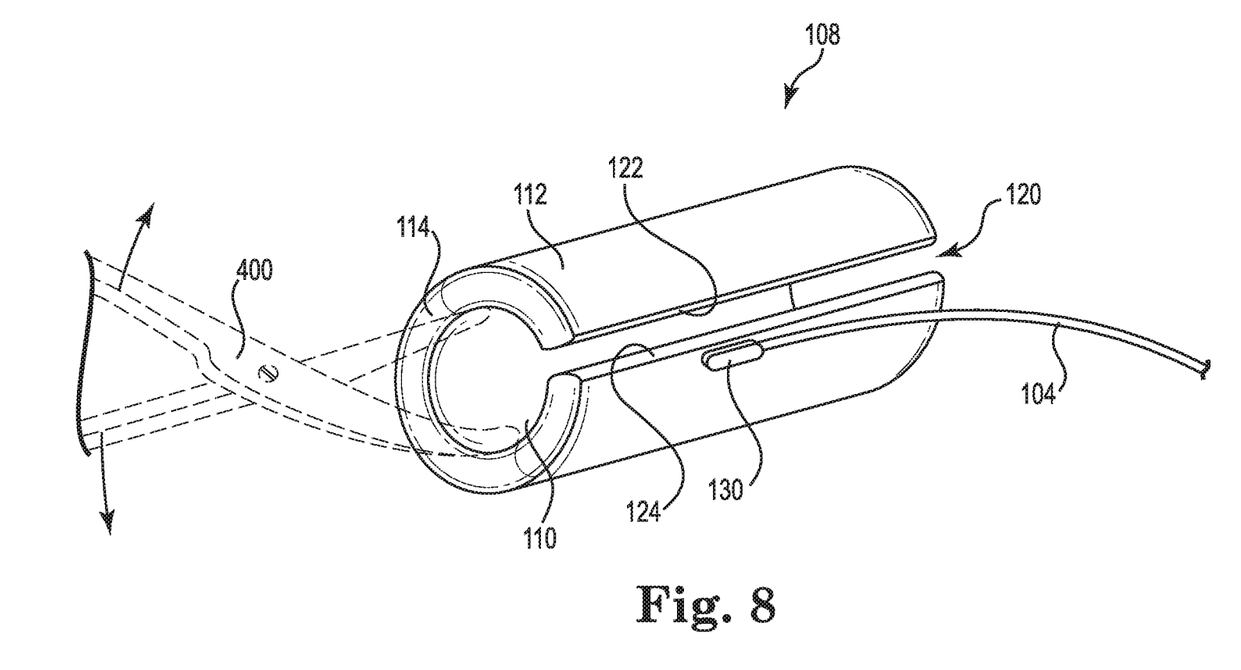
FIG. 8 is a perspective view of a surgical instrument inserted into and expanding the cuff illustrated in FIG. 2.

FIG. 8 is a perspective view of a surgical tool 400 employed to open the cuff 108 for placement around a urethra. The surgical tool 400 can include a forceps, a scissors, a blunt tip scissors, or the like that is inserted into the opening of the cuff 108 to apply pressure to the interior wall 110 to force the first face 122 away from the second face 124 to expand the part line 120. It is desirable to open the part line 120 a sufficient distance to allow the cuff 108 to be placed over the outside diameter of the urethra. The separable part line provides means for opening the circular shape of the cuff to allow placing the cuff around the urethra of the user. The cuff is fabricated to be pre-stressed or configured to have a memory that returns the cuff 108 to its circular (or closed) shape. Therefore, when the surgical tool 400 is removed the part line 120 closes.

Figure 9:
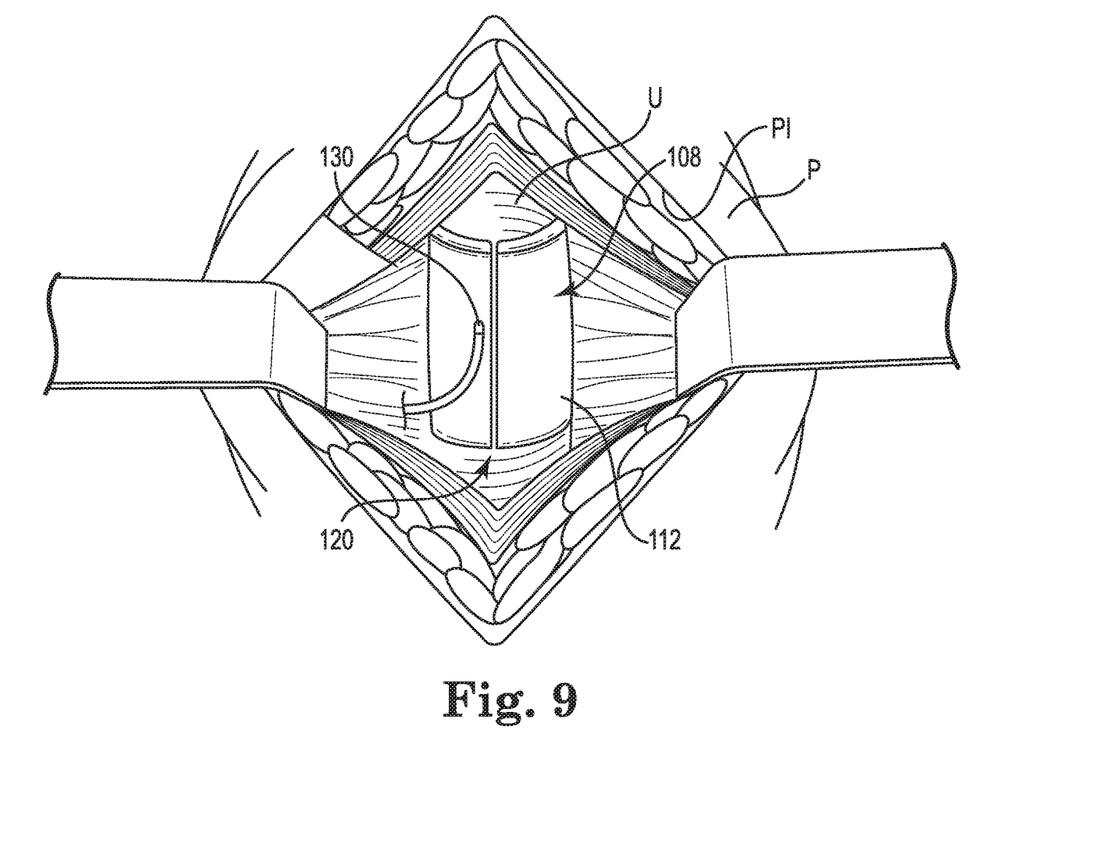
FIG. 9 is a schematic view of the cuff illustrated in FIG. 2 placed around the urethra of a patient.

FIG. 9 is a schematic view of a perineal incision PI formed to expose the urethra U, with the cuff 108 placed around the urethra U. The part line 120 has been expanded as described above and the cuff 108 has been positioned around the urethra U such that the connector 130 is accessible by the surgeon. In anatomical terms, the part line 120 and the connector 130 are located inferior relative to the urethra U between the perineum P and the urethra U.

With reference to FIG. 2 and FIG. 9 as descriptive examples, a method of treating a patient suffering from urinary incontinence includes a surgical procedure to implant the system 100. The patient is prepared for surgery in a manner described by the hospital or clinic policies or as supervised and approved by the surgeon. The perineal area of the patient is cleaned with suitable cleansers and prepared for surgery. A perineal incision PI is made on the midline of the patient, and tissue is dissected to expose the bulbospongiosus muscle supporting the urethra U. The surgeon will dissect laterally to free the fascia around the bulbospongiosus muscle and expose a portion of the bulbar urethra U. The bulbospongiosus muscle is immobilized, for example by clamping laterally to each side of the patient (FIG. 9), which exposes the urethra U for access by the surgeon. The surgeon dissects additional tissue and muscle by "tunneling" around the posterior side of the urethra U to create a pathway around a circumference of the urethra. The cuff 108 is opened in a manner as illustrated in FIG. 8 by separating the first face 122 from the second face 124 to expand the part line 120 enough to allow the urethra U to be surrounded by the cuff 108. The cuff 108 is placed around the urethra U with the connector 130 of the cuff 108 anterior to the urethra U. The cuff 108 is secured around the urethra U by sutures (FIG. 7) or a strap (FIG. 8). The connector 130 is attached to the tubing 104.

The surgeon typically confirms performance of the cuff 108 by injecting liquid into the connector 130 to fill the closed system 100, usually immediately prior to implantation of the system 100. The tubes 104 and the pump 102 are subsequently attached to the cuff 108. For example, the pump 102 is located in the scrotum (male) or labia (female) of the user and the tube 104 is connected between the pump 102 and the cuff 108 placed around the urethra U. The surgeon will pressurize the system 100 to the equilibrium pressure and cause the cuff 108 to coapt the urethra U. The surgeon will confirm that operation of the pump 102 will move liquid from the cuff 108 to the pressure-regulating reservoir 106, thus opening the urethra U and allowing the patient to pass urine. The surgical site is closed after confirmation of performance of the system 100.

Figure 10:
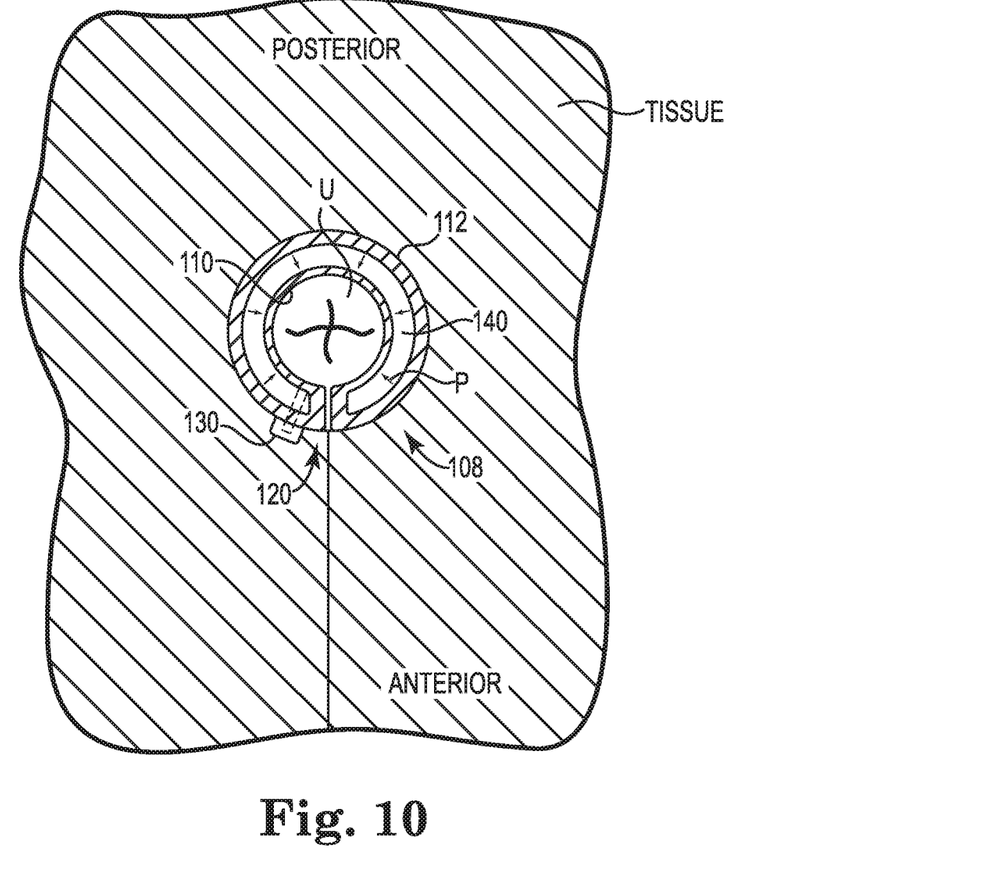
FIG. 10 is a schematic view of the cuff illustrated in FIG. 9 after implantation.

FIG. 10 is a schematic view of the cuff 108 after implantation and closing of the perineal incision PI. The part line 120 formed through the walls 110, 112 of the cuff 108 is located anterior relative to the urethra U such that the connector 130 is easily accessed by the surgeon during the surgical procedure. The system 100 illustrated in FIG. 2 is selectively operated by the user to inflate the cuff 108 to close the urethra (as shown in FIG. 10) or to deflate the cuff 108 to open the urethra to allow the passing or urine. In one embodiment described with reference to FIG. 2, the pressure-regulating reservoir 106 is filled and pressurized by the surgeon to a suitable pressure P upon implantation such that the system 100 maintains the urethra U in the closed position when the system 100 is in the steady state. The pressure-regulating reservoir 106 pressurizes the cuff 108 to close the urethra U and provide urinary continence for the user. The pressure P in the cuff 108 forces the wall 110 inward against the urethra U. The exterior wall 112 is thicker and stiffer and more resistant to deformation that the thinner interior wall 110, and as such, the wall 112 provides a backboard for supporting the movement of the interior wall 110. When the user desires to pass urine, the user squeezes the pump bulb 102 to move the liquid from the closed cavity 140 to the reservoir 106, which deflates the interior wall 110 of the cuff 108 and allows the passage of urine.

The wall 100 is configured to uniformly press against the urethra to smoothly coapt the urethra. FIG. 10 illustrates that pinching of the urethral tissue is reduced or eliminated with this design. The smooth and uniform nature of the wall 110, 112 configurations also reduces the likelihood of the cuff 108 forming a leak that can arise when inflatable AUS walls are bunched together, and this improved design reduces the possibility of cuff leakage from the cyclic use of the cuff 108 over many months.

Embodiments also include an alternative steady state in which the urethra U is open when the cuff 108 is in the steady state, and operation of the pump 102 operates to pressurize the cuff 108 and close the urethra.

Although specific embodiments have been illustrated and described in this patent application, it will be appreciated by those of ordinary skill in the art that a variety of alternate and/or equivalent implementations may be substituted for the specific embodiments shown and described without departing from the scope of the invention. This patent application is intended to cover any adaptations or variations of medical devices, as discussed above. Therefore, it is intended that this invention be limited only by the claims and their equivalents.

What is claimed is:

1. A cuff for an artificial urinary sphincter (AUS) system having a pressure reservoir attachable to a pump and a conduit attachable between the pump and the cuff, with the cuff comprising:

a one-piece monolithic polymer structure that is substantially circular in radial cross-section, the cuff having an interior wall connected by a pair of opposing end walls to an exterior wall such that the cuff forms a closed cavity located between the interior wall and the exterior wall and between the pair of opposing end walls;

a part line formed in the cuff and including a first face of the cuff that is separable from a second face of the cuff to allow the first face to be separated from the second face for placement of the cuff around a urethra of a user; and a connector in fluid communication with the closed cavity and configured to be connected to the conduit, wherein the connector is attached to the exterior wall adjacent one of the first face and the second face to provide access to the connector;

wherein, when the cuff is placed around the urethra of the user, liquid contained in the closed cavity is pressurized to an equilibrium pressure that is selected to maintain the cuff in a closed position around the urethra to provide the user with urinary continence.

2. The system of claim 1, wherein the cuff further comprises a tongue attached to the exterior wall adjacent to one of the first face and the second face and a keeper attached to the exterior wall adjacent to an other of the first face and the second face, the tongue insertable into the keeper to secure the cuff around the urethra of the user.

\* \* \* \* \*

UNITED STATES PATENT AND TRADEMARK OFFICE
CERTIFICATE OF CORRECTION

PATENT NO. : 11,033,376 B2  
APPLICATION NO. : 16/255837  
DATED : June 15, 2021  
INVENTOR(S) : Sarah J Schuchardt et al.

Page 1 of 1

It is certified that error appears in the above-identified patent and that said Letters Patent is hereby corrected as shown below:

In the Specification

In Column 2, Line 6, delete "in" and insert -- an --, therefor.

In Column 3, Line 19, delete "system 20." and insert -- system 30. --, therefor.

In Column 7, Line 16, delete "that" and insert -- than --, therefor.

In Column 7, Line 23, delete "wall 100" and insert -- wall 110 --, therefor.

Signed and Sealed this  
Twenty-sixth Day of October, 2021

Drew Hirshfeld  
*Performing the Functions and Duties of the*  
*Under Secretary of Commerce for Intellectual Property and*  
*Director of the United States Patent and Trademark Office*